United States Patent [19]

Fehr

[11] Patent Number: 4,647,407

[45] Date of Patent: Mar. 3, 1987

[54] UTILIZATION OF ETHYL 2-ACETYL-4-METHYL-4-PENTENOATE AS PERFUMING INGREDIENT

[75] Inventor: Charles Fehr, Versoix, Switzerland

[73] Assignee: Firmenich SA, Geneva, Switzerland

[21] Appl. No.: 784,125

[22] Filed: Oct. 4, 1985

[30] Foreign Application Priority Data

Oct. 18, 1984 [CH] Switzerland .......................... 4985/84

[51] Int. Cl.[4] ............................ A61K 7/46; C11B 9/00

[52] U.S. Cl. .................................. 252/522 R; 568/397

[58] Field of Search ...................... 252/522 R; 568/397

[56] References Cited

U.S. PATENT DOCUMENTS 4,245,122 1/1981 Yoshida et al. ..................... 568/397

OTHER PUBLICATIONS

Wood et al., "J. Organic Chem.", vol. 28, (1963), p. 2248.

Bowie et al., "J. Amer. Chem. Soc.", vol. 87, pp. 5742–5746 (1965).

Burdet et al., "J. Amer. Chem.", vol. 86 (1964), pp. 2105–2108.

*Primary Examiner*—Werren B. Lone

*Attorney, Agent, or Firm*—Pennie & Edmonds

[57] ABSTRACT

Ethyl 2-acetyl-4-methyl-4-pentenoate develops a fruity-flowery, aromatic, faintly herbaceous scent of natural character and consequently can be used advantageously in numerous fragrance compositions of different nature and to impart a distinct odor to consumable materials.

3 Claims, No Drawings

UTILIZATION OF ETHYL 2-ACETYL-4-METHYL-4-PENTENOATE AS PERFUMING INGREDIENT

BRIEF SUMMARY OF THE INVENTION

The present invention provides a method to confer or enhance the fragrance properties of consumable materials which method consists in adding thereto an odor effective amount of ethyl 2-acetyl-4-methyl-4-pentenoate.

The present invention provides further a fragrance composition which comprises having added thereto an odor effective amount of ethyl 2-acetyl-4-methyl-4-pentenoate.

This invention provides also a perfumed consumable material having added thereto an odor effective amount of ethyl 2-acetyl-4-methyl-4-pentenoate.

BACKGROUND OF THE INVENTION

Ethyl 2-acetyl-4-methyl-4-pentenoate is a known chemical entity. It has been described by T. F. Wood et al. [see J. Org. Chem. 28, 2248 (1963)] as a synthesis intermediate in a process for the preparation of certain aromatic musks. Its odorous properties however have remained so far unrecognized. I have now discovered that this ester possesses very useful fragrance characters and consequently it can be utilized in a wide range of applications.

THE INVENTION

Ethyl 2-acetyl-4-methyl-4-pentenoate possesses a fruity-flowery, aromatic, faintly herbaceous scent of natural character. Its odor is reminiscent of certain aspects of the odor developed by camomile decoction and of the fruity charcter of pineapple.

Different consumable materials can be perfumed by the pentenoate ester of the invention. These include soaps, cosmetics, shampoos, body deodorizes, air fresheners, fabric softeners, liquid or solid detergents, of either cationic, anionic, non ionic or zwitterionic type. Ethyl 2-acetyl-4-methyl-4-pentenoate possesses a good stability toward different aggressive media and shows good substantivity on fabrics of both natural and synthetic origin.

The proportions at which the pentenoate ester of the invention can be used to achieve the desired results vary within a wide range of values. Concentrations of the order of 1 or 2–5% by weight based on the total weight of the given composition into which it is added can be utilized. Such concentration values, or even lower, can perfectly satisfy the normal requirements in the perfuming of articles such as soaps, detergents, cosmetics or shampoos.

It is apparent to those skilled in the art that these values of concentration depend on the nature of the materials it is desired to perfume or of the coingredients present in a given composition and, of course, of the specific effects one desires to achieve.

Ethyl 2-acetyl-4-methyl-4-pentenoate can be employed by directly adding it to the composition or consumable material it is desired to perfume or, more conveniently, in admixture with other current perfume coingredients. As an example of suitable current coingredients of natural or synthetic origin, one may cite those compounds described in European patent application published under No. 0096243. As mentioned above, ethyl 2-acetyl-4-methyl-4-pentenoate is a known chemical entity. It can be prepared from ethyl acetoacetate by reaction with methallyl chloride in a basic medium according to the following reaction scheme:

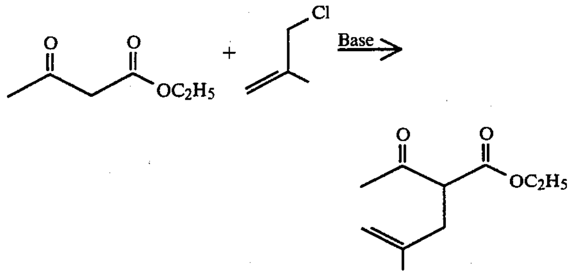

The reaction is preferably carried out in an aqueous, an aqueous alcoholic or alcoholic medium, more preferably in ethanol. Other suitable inert organic solvents include acetone or an aromatic hydrocarbon such as benzene, toluene or xylene.

Suitable basic agents include alkali metal alkoxides, e.g. sodium ethoxide, sodium, lithium or potassium carbonate or a hydroxide, for instance potassium hydroxide.

For practical and economical reasons potassium carbonate is preferred and the reaction is carried out in ethanol. Under these conditions, the reaction is effected at the boiling temperature of the reaction mixture, i.e. at about 75° C. According to the chosen solvent, the reaction temperature can be of between about 50° and 110° C. At these temperature values, the reaction time is relatively short and the formation of by-products is reduced. The preparation of ethyl 2-acetyl-4-methyl-4-pentenoate, as well as its utilization according to the invention, will be illustrated in a more detailed manner in the following example wherein the temperatures are indicated in degrees centigrade and the abbreviations have the meaning common in the art.

EXAMPLE 1

Preparation of ethyl 2-acetyl-4-methyl-4-pentenoate

In a reaction vessel of 1.5 l equipped with a mechanical stirrer, a condenser, a thermometer and an inlet tube for nitrogen, 600 g (4.61M) of ethyl acetate, 375.9 g (4.15M) of methallyl chloride, 500 ml of ethanol and 636.9 g (4.61M) of potassium carbonate are mixed together. The resulting suspension is heated at reflux for 2 h while the mixture becomes slightly yellow and thick. Ethanol is stripped off and the obtained residue is dissolved in 900 ml of water. The two layers thus formed are separated and the organic phase is washed with 900 ml of water.

The raw material (740 g) is distilled under nitrogen over a column filled with stainless steel turnings by making use of a distillation head at total reflux. 555.8 G of the desired keto-ester are thus obtained.

B.p. 115°/$2.66\times10^3$ Pa (yield by weight 107%; theor. 75%).

EXAMPLE 2

Perfume composition

A base perfume composition for shampoos was prepared by mixing the following ingredients (parts by weight):

| | |
|---|---|
| synth. Linalol | 180 |

-continued

| | |
|---|---|
| Phenoxyethyl isobutyrate | 150 |
| Phenethylol | 100 |
| Hydratropic alcohol | 70 |
| Benzyl salicylate | 60 |
| Methyl cresotinate 10%* | 50 |
| Allyl phenoxyacetate 10%* | 40 |
| Benzyl acetate | 30 |
| Lilial[1] | 30 |
| α-Damascone[2] 10%* | 20 |
| Mayol ®[2] [3] | 20 |
| Hedione[2] [4] | 20 |
| synth. Geranium oil | 20 |
| Veloutone[2] [5] | 20 |
| β-Damascenone 1%* | 20 |
| α-Hexylcinnamic aldehyde | 20 |
| Musk DTI[2] [6] | 10 |
| | 860 |

*in diethyl phthalate
[1]L. Givaudan, Vernier (Switzerland)
[2]Firmenich SA, Geneva (Switzerland)
[3]4-isopropyl-cyclohexylmethanol
[4]methyl dihydrojasmonate
[5]2,5,5-trimethyl-2-pentyl-cyclopentanone
[6]1,1-dimethyl-4-acetyl-6-tert-butylindane By adding to the above base 140 g of ethyl 2-acetyl-4-methyl-4-pentenoate, a novel composition is obtained with a distinct flowery-fruity, aromatic and herbaceous scent reminiscent of the natural odor of a herb decoction. This odor character renders the composition particularly adapted to the perfuming of shampoos or hair conditioning articles.

EXAMPLE 3

Two powder detergent bases were prepared by mixing the following ingredients (parts by weight):

| | Composition | Composition with sodium perborate |
|---|---|---|
| Sodium linear alkyl-benzenesulphonate (chain length: $C_{11-5}$) | 8.0 | 6.4 |
| Ethoxylated tallow alcohol (14EO) | 2.9 | 2.3 |
| Sodium soap (chain length: $C_{12-16}$ 13–26%; $C_{18-22}$ 74–87%) | 3.5 | 2.8 |
| Sodium triphosphate | 43.8 | 35.0 |
| Sodium silicate | 7.5 | 6.0 |
| Magnesium silicate | 1.9 | 1.5 |
| Carboxymethylcellulose | 1.2 | 1.0 |
| Sodium EDTA | 0.2 | 0.2 |
| Sodium sulphate | 21.2 | 17.0 |
| Water | 9.8 | 7.8 |
| Sodium perborate | — | 20.0 |
| | 100.0 | 100.0 |

By adding to a sample of each of the above detergent bases 1% of ethyl 2-acetyl-4-methyl-4-pentenoate, there were obtained two novel compositions having an agreeable fresh and herbaceous scent.

EXAMPLE 4

By using ethyl 2-acetyl-4-methyl-4-pentenoate at the concentrations indicated, the following consumable materials were perfumed:

| | concentration [%][1] |
|---|---|
| Lotion | 5.0 |
| Night cream | 0.4 |
| Shampoos | 0.5 |
| Deodorant (aerosol) | 1.2 |
| Hair lacquer | 0.3 |
| Soap[1] | 0.5 |
| Talc | 0.5 |
| Chlorinated dish-washing detergent powder | 0.2 |

[1]Type: LUX, Unilever Ltd.

The products thus perfumed presented an agreeable flowery-fruity scent. The odor was stable as indicated by storage of samples of the perfumed materials over a period of 1 month at 40°.

What I claim is:

1. A method to confer or enhance the fragrance of soap, cosmetics, shampoo, body deodorizer, air freshener, fabric softener, liquid detergent, or solid detergent which consists in adding thereto an odor effective amount of ethyl 2-acetyl-4-methyl-4-pentenoate.

2. A consumable material selected from perfumes, soaps and detergents containing as an effective odor ingredient ethyl 2-acetyl-4-methyl-4-pentenoate.

3. A perfuming composition having added thereto an odor effective amount of ethyl 2-acetyl-4-methyl-4-pentenoate.

* * * * *